(12) United States Patent
Baumbach (10) Patent No.: US 10,470,672 B2
(45) Date of Patent: Nov. 12, 2019

(54) MEASUREMENT OF BLOOD PRESSURE

(71) Applicant: EPITHERM LIMITED, Bishop's Stortford, Hertfordshire (GB)

(72) Inventor: Per Baumbach, Bishop's Stortford (GB)

( * ) Notice: Subject to any disclaimer, the term of this patent is extended or adjusted under 35 U.S.C. 154(b) by 198 days.

(21) Appl. No.: 15/556,312

(22) PCT Filed: Mar. 9, 2016

(86) PCT No.: PCT/GB2016/050644
§ 371 (c)(1),
(2) Date: Sep. 7, 2017

(87) PCT Pub. No.: WO2016/151281
PCT Pub. Date: Sep. 29, 2016

(65) Prior Publication Data
US 2018/0092553 A1    Apr. 5, 2018

(30) Foreign Application Priority Data

Mar. 25, 2015   (GB) .................................. 1505018.0

(51) Int. Cl.
*A61B 5/022* (2006.01)
*A61B 5/026* (2006.01)
*A61B 5/1491* (2006.01)
*A61B 5/1477* (2006.01)

(52) U.S. Cl.
CPC .......... *A61B 5/02233* (2013.01); *A61B 5/026* (2013.01); *A61B 5/1491* (2013.01); *A61B 5/02208* (2013.01); *A61B 5/1477* (2013.01)

(58) Field of Classification Search
CPC ... A61B 5/02233; A61B 5/026; A61B 5/1491; A61B 5/1477; A61B 5/02208
See application file for complete search history.

(56) References Cited

U.S. PATENT DOCUMENTS

| 4,290,431 A * | 9/1981 | Herbert ................ G01N 27/404 |
| | | 204/403.06 |
| 4,776,339 A * | 10/1988 | Schreiber ........... A61B 5/02255 |
| | | 600/324 |
| 2008/0081963 A1 | 4/2008 | Naghavi et al. |
| 2010/0049007 A1 | 2/2010 | Sterling et al. |
| 2010/0324429 A1* | 12/2010 | Leschinsky ........ A61B 5/02208 |
| | | 600/493 |
| 2013/0184745 A1 | 7/2013 | Leschinsky |

FOREIGN PATENT DOCUMENTS

| EP | 0077073 A2 | 4/1983 |
| GB | 1461345 A | 1/1977 |

OTHER PUBLICATIONS

European Patent Office, Written Opinion of the International Searching Authority on PCT/GB2016/050644, dated Jul. 1, 2016, NL—2280 HV Rijswijk.
European Patent Office, International Search Report, of the International Searching Authority on PCT/GB2016/050644, dated Jul. 1, 2016, NL—2280 HV Rijswijk.

* cited by examiner

*Primary Examiner* — Eric F Winakur
*Assistant Examiner* — Chu Chuan Liu
(74) *Attorney, Agent, or Firm* — Louis Ventre, Jr.

(57) ABSTRACT

Disclosed is a blood pressure measurement device comprising a heat flow perfusion sensor in combination with occlusion means for restricting the flow of blood in a portion of a human or animal body.

19 Claims, 8 Drawing Sheets

MEASUREMENT OF BLOOD PRESSURE

FIELD OF THE INVENTION

This invention relates to apparatus comprising a perfusion sensor or meter for use in measuring the blood pressure ("BP") of a human or animal subject, a method of making the apparatus, and to a method of measuring blood pressure using the apparatus.

BACKGROUND TO THE INVENTION

The method routinely used by clinicians to measure blood pressure in humans is well-known and requires the use of a sphygmomanometer, in combination with a stethoscope or, in the case of automated BP-measuring devices, electronic means to determine the Korotkoff sounds during the measurement. Whilst this method is non-invasive, it does not permit truly continuous monitoring of blood pressure in real time over prolonged periods providing, at best, intermittent blood pressure values.

Clinically, it is conventional to monitor the "mean arterial pressure" or MAP. The MAP is derived from the values for systolic and diastolic pressures according to the equation:

$$MAP = P_d + \frac{1}{3}(P_s - P_d)$$

Where $P_d$=diastolic pressure and
$P_s$=systolic pressure

There are many situations in which continuous monitoring of blood pressure is desirable, especially in operating theatres and in Intensive Care Units. The sphygmomanometer is not adequate in such situations, and conventionally an intra-arterial pressure catheter is used. However this is invasive and therefore not ideal. There is thus a need for an improved apparatus and method for non-invasive measurement of blood pressure, especially one which allows for substantially continuous monitoring to be made in a simple and non-labour intensive manner.

There have been many attempts to obtain a reliable estimate of arterial pressure using methods based on existing non-invasive tissue perfusion techniques: plethysmograms, photoplethysmograms ("PPG"), acoustic and optical Doppler techniques, CT/PET scanning methods, etc. using ever more advanced equipment and signal analysis (see e.g. http://en.wikipedia.org/wiki/Continuous_noninvasive_arterial_pressure).

Thus, whilst excellent clinical insights have been published no simple, practical solution to this problem has been developed. The main reason is that even though in theory, the rate of peripheral perfusion (that is, the volume of blood supplied, in millilitres, per 100 grams of perfused tissue, per minute) is proportional to the supplying blood pressure, in practice its measurement is far from simple due to the intrinsically complex anatomical and neurological autoregulatory nature of human tissue.

In purely mathematical terms, the multi-directional blood flow through the human skin's 3-dimensional and constantly (auto-)varying vessel diameters, opening/closing of anastomoses, etc. can best be described as a chaotic system. Further, the number and density of blood vessels varies greatly between different skin locations (e.g. there are over 140 capillary loops per $mm^2$ on the forehead, but only about 40 per $mm^2$ on the calf, [Ryan T J. The Physiology and Pathophysiology of the Skin *New York Academic Press* 1973, pp 571-651]). Dynamic measurements of single factors, e.g. blood volume or blood cell velocity can only at best give a "perfusion index"—which even then is fraught with uncertainty. Further, existing apparatus and methods use measurement sites (finger, wrist etc.) that are highly susceptible to movement artefacts.

The present invention aims to provide an apparatus and method which ameliorates or overcomes at least some of the problems experienced with the known apparatus and methods and to provide a simple, safe, inexpensive, yet reliable continuous non-invasive Mean Arterial Pressure ("cMAP") measurement.

SUMMARY OF THE INVENTION

In a first aspect, the invention provides a blood pressure measurement device comprising a heat flow perfusion sensor in combination with occlusion means for restricting the flow of blood in a portion of a human or animal body.

Conveniently the occlusion means comprises an inflatable cuff, typically generally of the sort well-known from conventional sphygmomanometers, except modified to include a perfusion sensor as described herein. Accordingly the cuff will generally be adapted and configured to fit around the arm of a human subject and, when inflated to a necessary extent, will occlude at least some of the blood vessels (more especially, at least some of the arteries) in the subject's arm.

It will be apparent to those skilled in the art however that the invention is not restricted to use with human subjects and could instead be used with non-human subjects, especially rare or valuable animals such as zoo animals, race horses, etc., where extensive veterinary care is appropriate. The occlusion means may be adapted and configured therefore, in certain embodiments, for use with such animals.

Equally, the occlusion means may be provided in various sizes to fit different human subjects. For example, a very small cuff may be used to fit a baby or child, whilst a larger than normal cuff may be used for e.g. obese adults. The size of the perfusion sensor may be adjusted in accordance with the size of the occlusion means. As a guide, a perfusion sensor for a normal human adult may typically have a maximum width (typically, a diameter) of about 2-2.5 cm; a perfusion sensor for a baby may typically have a maximum width of about 1 cm; whilst a perfusion sensor for an obese adult may typically have a maximum width of about 5 cm.

The perfusion sensor in the device of the invention is a heat flow perfusion sensor (i.e. one in which inter alia, heat loss from the sensor due to convection by blood flow in the subject is used to measure perfusion and where the convection heat loss can preferably be temporarily prevented by occluding the subject's vasculature (especially the arteries) in the region of the sensor. Alternatively stated, a heat flow perfusion sensor is one in which measurement of perfusion is based on the clearance or removal of thermal energy from the sensor by blood replenishment in a volume of tissue (the sensor preferably being heated to a temperature above normal skin temperature).

A generally suitable sensor is fully described in U.S. Pat. No. 4,539,994 (the content of which is incorporated herein by reference).

The device of the invention may comprise an integral digital processing member or element (more especially an electronic digital processing means, such as a microprocessor, microcontroller or the like) to calculate a determined subject blood pressure from a signal or reading output from the perfusion sensor. Alternatively, the device may be placed in operable connection with an external electronic digital signal processing means e.g. by a wired connection, or by a wireless connection, such as near field communication, Bluetooth® or WiFi® connection or the like, such that a signal or reading output from the perfusion sensor can be processed by the external signal processing means.

In preferred embodiments the perfusion sensor is in integral physical combination with the occlusion means. It will be appreciated that where the perfusion sensor is a heat flow perfusion sensor, it is necessary to establish good thermal contact between the sensor and the skin of the subject. Accordingly the sensor will preferably be integrated into an inflatable cuff or similar occlusion means such that, in use, the perfusion sensor is substantially in direct thermally-conducting contact with the skin of the subject. Thus, for example, the perfusion sensor may conveniently be located at the inner surface of a cuff such that, when the cuff is wrapped around a subject's arm, the sensor lies adjacent the skin of the subject.

In the device of the invention, the perfusion sensor will typically comprise temperature regulation means, which desirably includes at least a heating means (such as an electrical element) and preferably also a thermostat or other temperature control or measurement means, such as a temperature dependent switch or measurement device including, but not restricted to, PTC or NTC resistors, IC temperature sensors, etc. The sensor comprises at least one portion which is in good thermally-conducting contact with the surface of the subject, and which is thermally-insulated from the ambient environment. At least that portion of the sensor which is in good thermally-conducting contact with the surface of the subject will typically, during use, be heated to a temperature above the skin surface temperature of the subject. For humans, whilst the central core or deep body temperature is about 37 to 37.5° C., the normal temperature at the surface of the skin is about 32° C. Other portions of the sensor may preferably be similarly heated, so as to thermally isolate the subject-contacting portion from the ambient environment.

While heat loss or "heat clearance" measurements can be performed at temperatures (e.g. 34-37° C.) only slightly elevated relative to skin surface temperatures, this gives sensor signals that are close to, or below, the physiological "noise floor" with ensuing reduced clinical reliability. The sensor system operates especially well at a temperature range from 39 to 45° C., with 41 to 42° C. being preferred, as representing a good compromise between sensor signal sensitivity on the one hand and patient comfort and convenience and skin burn prevention during prolonged monitoring on the other.

Figure 2:
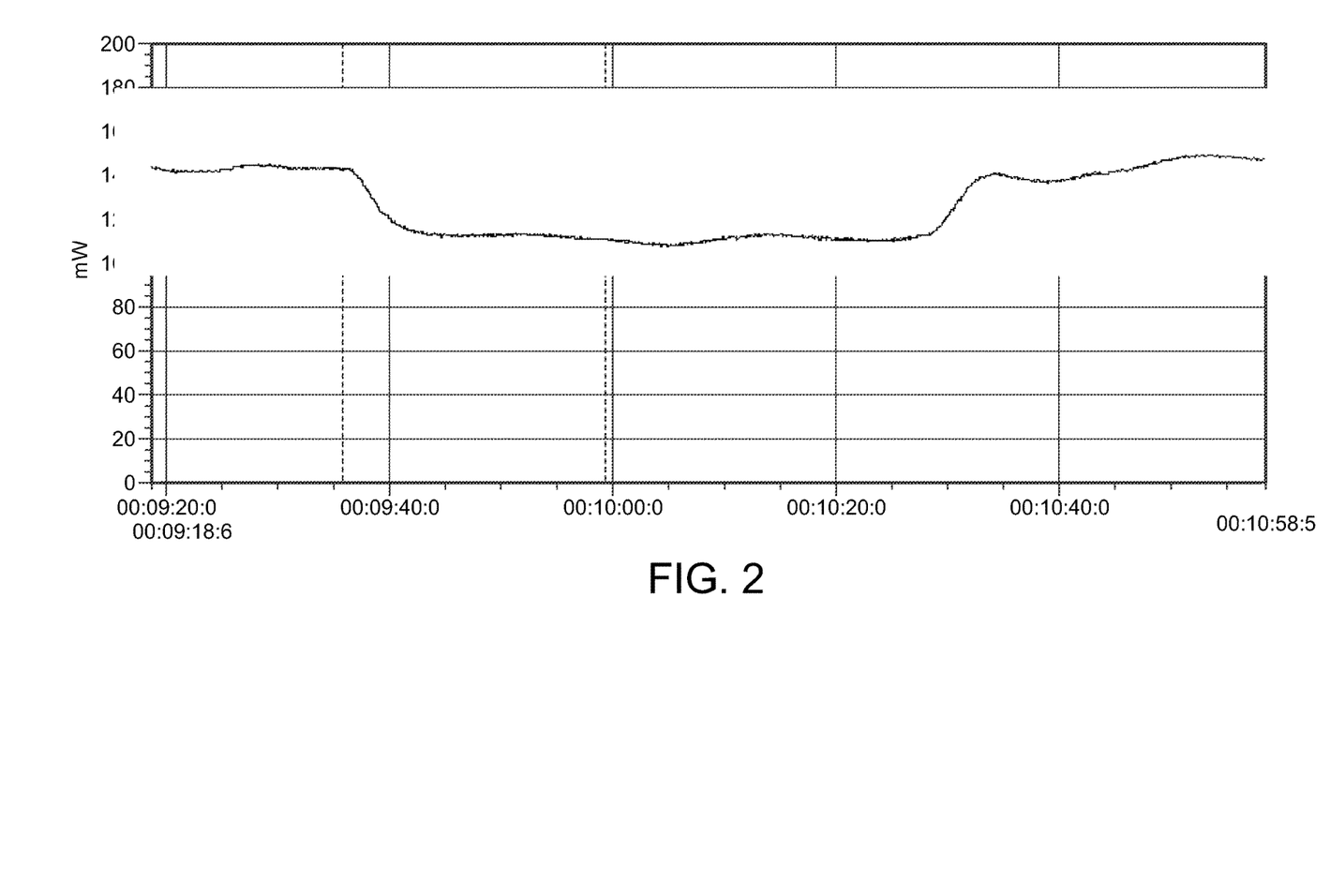
FIG. 2 is a graph of mW (milliwatts) against time, obtainable using a device in accordance with the invention.
Figure 3:
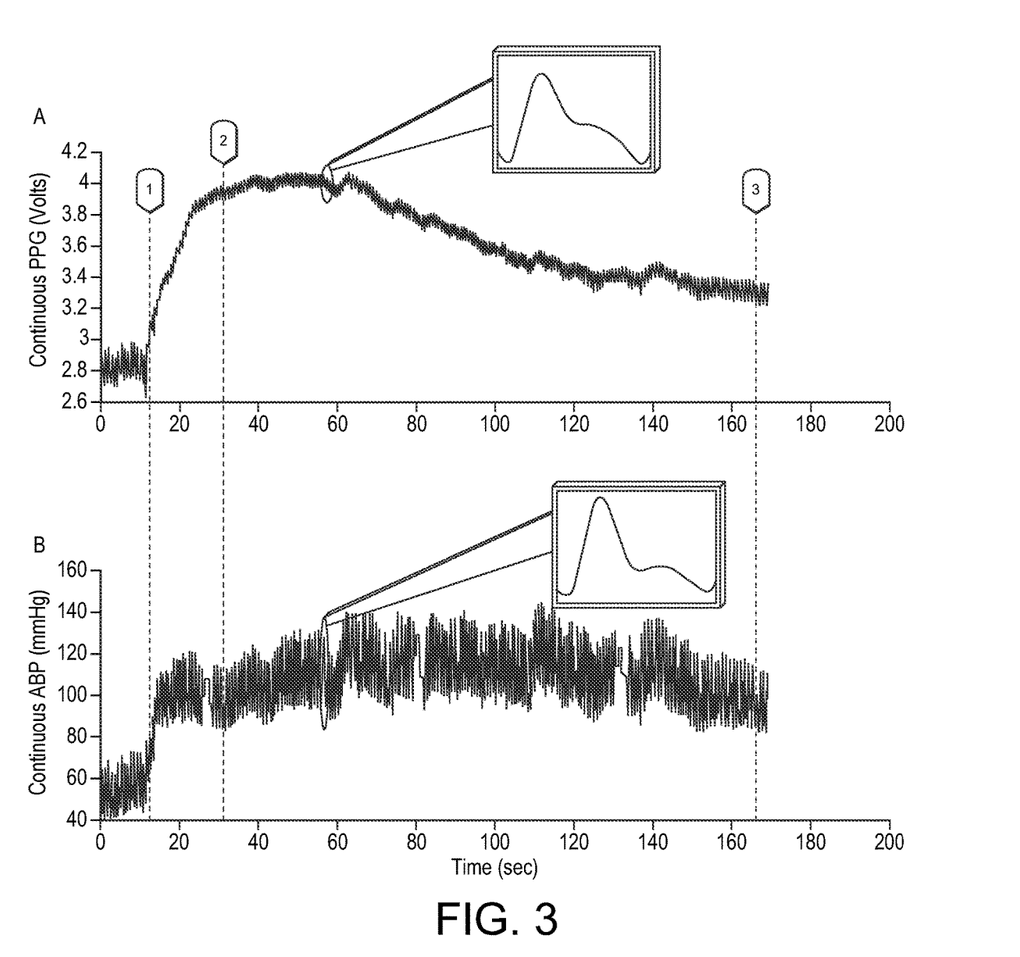
FIG. 3A is a graph of volts against time, obtained using a conventional PPG instrument.
FIG. 3B is a graph of arterial blood pressure (mmHg) against time (seconds)

A second advantage of operating at this temperature elevation is that significant parts of the normal vascular auto-regulation complex (e.g. opening and closing of arterial-venous anastomosis shunts, blood vessel compliance changes etc.) are solidly overridden by the dominating thermal hyperaemia reaction. This is illustrated in FIGS. 2 & 3 (described in detail in the Examples below) which show that the suggested heat clearance measurement stays stable and proportional to the local blood pressure while the PPG reflects a return drift, in both baseline value as well as PPG waveform amplitude, due to vascular mechanisms other than BP, rendering it unsuitable for continuous monitoring of BP (Reisner A. et al., Utility of the Photoplethysmogram in Circulatory Monitoring *Anaesthesiology* 2008, 108 p 950-958).

Human skin has two independent systems for regulating peripheral blood flow/perfusion: a vasoconstrictor system and a sympathetic active vasodilator system. These are under control from both the central nervous system and local neural networks and constantly adjust the perfusion to help maintain homeostasis, including maintenance of body temperature (thermoregulation) and blood pressure (baroreflex) respectively). Thus, in normothermic conditions, there is no certain or direct relation between actual skin perfusion and blood pressure.

In preferred embodiments, the present invention comprises a heated perfusion sensor that increases the local skin temperature, triggering the dominating vasodilator system. The resulting establishment of a local hyperperfusion effectively overrides all other neural perfusion control inputs and provides a low vascular resistance that allows a direct correlation between the perfusion and the forcing mean arterial blood pressure.

In a preferred embodiment the sensor comprises a peripheral or outer portion and an inner portion. The peripheral or outer portion conveniently comprises a substantially annular portion and the inner portion desirably comprises a substantially circular flattened disk. More especially the outer portion advantageously comprises an inverted cup-shaped shield around the inner portion, the cup-shaped shield being formed from an annular ring and a lid.

It is a highly preferred feature of the invention that the inner portion is mounted in the sensor by resiliently deformable mounting means which allows for some movement of the inner portion relative to the outer portion. There are many ways of achieving this. In one embodiment the inner portion comprises or is attached to a flexible support, which flexible support is in turn typically anchored or attached to the outer portion. Conveniently this may be disposed in a ring around the inner portion, between the inner and outer portions. Another method involves the use of one or more soft springs between the inner portion and a lid part of the outer portion, which one or more soft springs gently urge the inner portion downwards. In some embodiments both an annular flexible support and one or more soft springs may be present.

Suitable materials for use as a flexible support typically include elastomeric polymeric materials such as silicone rubber, especially liquid silicone rubber ("LSR"), VMQ silicone rubber, nitrile butadiene rubber (a copolymer of acrylonitrile and butadiene), also known as NBR, hydrogenated nitrile butadiene rubber ("HNBR"), FKM and FFKM fluoroelastomers and the like. These materials are widely available commercially.

To avoid compression of the subject's capillary bed it is necessary to apply a pressure lower than the normal capillary pressure of about 43 mmH$_2$O or 0.0043 N/mm$^2$. The area of the central portion of the sensor is typically around 5×5×Pi [mm$^2$], so the max pressure is about 0.3 [N]. Allowing 1 mm sensor movement, the minimum suspension compliance (Cms) should thus be [3 mm/N].

The suspension compliance is measured in metres/Newton, and thus indicates the amount of movement for a given force. An upper limit for the compliance of the inner portion of the sensor will typically be about 9-10 mm/N.

The object of the resiliently deformable mounting is to provide a substantially constant and low pressure contact between the inner portion of the sensor and the subject's skin. Several advantages stem from this. Firstly, previous heat flow sensors (such as the type disclosed in U.S. Pat. No. 4,539,994) have had the central, inner sensor portion solidly mounted (e.g. by potting in epoxy resin or the like). As a result, they have suffered from inaccuracies in measurement due to artefacts from the skin attachment means (e.g. adhesive tape, or elastic bands or the like) which have either been too loose, giving poor thermal contact, or too tight (or subject to external pressure), thus compressing or even occluding the underlying vascular bed in the subject.

A second advantage is that the resiliently deformable mounting enables the sensor to function as a stethoscope, with the compliant, deformable mounting acting as a diaphragm to register low frequency Korotkoff sounds (which are essentially skin pulsations caused by volume changes in the arteries).

A third advantage of the resiliently deformable mounting is that it enables for improved response times for the Emin curve fit prediction (e.g. as described in Example 6 below), by avoiding deformation of the underlying skin volume and associated distortion of the mW signal decay.

Occlusion of the blood flow will tend to have different effects on the core tissue temperature of a body extremity, depending on the tissue location relative to the area of occlusion. Thus, the tissue located downstream of an area of occlusion will tend to cool down, due to the cessation of relatively warm incoming arterial blood. Conversely, the tissue located upstream of an area of occlusion will tend to warm up slightly, due to the lack of returning, relatively cool, venous blood. Although these effects are small, they are preferably avoided by having the perfusion sensor in the device of the invention positioned at a "thermally neutral" location (i.e. one in which the temperature of the sensor is substantially unaltered by the aforesaid phenomena). In the present instance, where the occlusion means comprises an inflatable cuff, the perfusion sensor is preferably positioned immediately distal to the inflatable portion of the inflatable cuff (i.e. further from the heart). This is explained further in Example 7 below.

In preferred embodiments the device of the invention comprises a microphone or other acoustic sensor. The microphone or other acoustic sensor may be used, for example, to detect Korotkoff sounds during activation and deactivation of the occlusion means (e.g. during inflation and deflation of a cuff). The output from the microphone or other acoustic sensor is typically fed to a digital signal processing member which conveniently is mounted on, and forms an integral component of, the device of the invention.

The microphone or acoustic sensor preferably forms an integral part of the device of the invention. It may, however, in some embodiments, be provided as an external component which is placed in operable relationship with the occlusion means. For example, in some conventional sphygmomanometers, a microphone is operably associated with an inflatable cuff via the tubing used to inflate the cuff. The blood pressure determined by such conventional "acoustic" means may be used to calibrate the mean arterial pressure readings obtained using the perfusion sensor.

In preferred embodiments the device of the invention may include one or more other sensors in addition, or as an alternative, to the microphone or acoustic sensor mentioned above. In particular, for example, the device of the invention may comprise means to detect and/or measure the pulsatile blood pressure waveform. Conveniently the device of the invention may include sensors and associated components for performing a photoplethysmogram (PPG) and/or to conduct pulse oximetry (especially reflective pulse oximetry, as opposed to transmissive pulse oximetry). To this end, the device of the present invention may advantageously comprise at least one light source, more preferably at least two light sources. The light source or sources are typically LEDs. In one embodiment two different LEDs are provided, which illuminate the patient's skin, each with light of a different respective range of wavelengths or peak wavelength. It will be apparent to those skilled in the art that the device of the invention will advantageously further comprise at least one light sensor e.g. to detect light reflected from the subject. The light sensor conveniently comprises a photodetector, such as a photodiode.

More especially, the one or more additional sensors which the device of the invention may comprise, are preferably mounted on or close to the perfusion sensor, such that one or more of the electronic components optionally operably associated with the perfusion sensor (especially the digital signal processing means) may also be operably associated with the one or more additional sensors, so as to provide maximum economy of components.

In a particular embodiment, the device of the invention is adapted and configured to provide substantially continuous monitoring of the blood pressure, more especially the continuous mean arterial pressure (or "cMAP"), of a subject. This is very important for early detection of intra- and post-operative circulatory shock ("CS"). Circulatory shock is the most common condition that leads to a fatal outcome in the OR/ICU, in particular septic shock which amounts to over 750,000 cases in the US alone every year.

A definite clinical indication of the onset of CS is systemic arterial hypotension, but the drop in blood pressure may be only moderate, especially in patients with chronic hypertension. However, another early clinical sign of CS is a drop in tissue perfusion which leads to cold and clammy skin appearance.

Rather than appearing as yet another number on a monitor screen, the perfusion measurement could be depicted as a graphical balance meter or "Circulation stability indicator". If this moves out of a "green" or permissible central zone, an alarm is given and an extra cuff inflation and BP measurement is automatically triggered. The proposed BP measurement device would thus provide an early warning of the onset of CS, long before the change in skin appearance can be asserted by clinical observation. Conversely, if the "Circulation stability indicator" shows a stable circulatory condition, the planned next cuff inflation can be delayed or omitted for increased patient comfort.

Further, with information on both blood pressure and perfusion it is simple to calculate real-time effective vascular resistance ("Vreff") (or compliance ("Vceff")) which is highly desirable in certain clinical settings, but not currently available in routine clinical practice. (Vreff=BP/perfusion whereas Vceff=perfusion/BP)

The invention provides, in a second aspect, automated apparatus for monitoring the blood pressure of a human or animal subject, the apparatus comprising a device in accordance with the first aspect of the invention, and automated means for actuating the occlusion means of the device. The automated means for actuating the occlusion means of the device may, in some embodiments, be integrated into the device. More conveniently, the automated means is separate from the device but functionally or operably connected thereto. For example, where the occlusion means comprises an inflatable cuff, the automated actuation means may comprise a hydraulic pump or air pump, connected to the cuff by a fluid-tight tube or hose.

The automated actuation means may be provided with an integral power source (such as a battery) or may be provided with an external power source, such as a mains electrical power supply.

Desirably the automated actuation means may be triggered to actuate the occlusion means as a result of any one of two or more distinct trigger events. Typically, the automated actuation means may be triggered by a clock or elapsed time counter. For example, the actuation means may be configured so as to cause inflation of a cuff or other occlusion means after a pre-determined period of time has elapsed. The length of the pre-determined period is preferably adjustable (e.g. by a clinician, anaesthetist, theatre nurse or the like) according to the clinical context. A typical time period may be in the range 3 minutes to one hour or so, depending on the circumstances.

Desirably the automated actuation means may also be triggered to actuate the occlusion means by operation of a manual override and/or if a cMAP reading taken by the device falls outside (above or below) an acceptable range. Conveniently the apparatus of the second aspect provides a signal output which can be fed into a computer or other digital electronic control apparatus. The output from the apparatus may helpfully be indicated visually e.g. on a display monitor. If the subject cMAP determined by the device or apparatus falls outside the acceptable range, the actuation means may be triggered, so that a further subject BP measurement can be made, and a visual warning can be indicated on the display (if present). Additionally, or alternatively, an audible warning alarm can be triggered by the apparatus. If desired, the apparatus can send a signal (e.g. by wireless communication means) to trigger a remotely-situated alarm (e.g. at a nurses' station in an ICU).

Conversely, in some embodiments, if the measured cMAP continues to fall within an acceptable range, an output or signal from the perfusion sensor may override a scheduled cuff inflation (or other arterial occlusion event) if such is due according to a predetermined time interval. Thus, cuff inflations which are unnecessary (because the subject's blood pressure is stable within an acceptable range) can be avoided. One advantage of this is greater comfort and convenience for the subject especially if, for example, they are trying to sleep.

The apparatus of the second aspect of the invention will typically comprise a housing, in or on which may conveniently be provided those components which are commonly found in conventional automated sphygmomanometers. These include, for example, cuff inflation means, as aforesaid, a microprocessor or microcontroller, a power source (especially an integral battery or the like), a graphical display means and the like. A commercially available automated sphygmomanometer which may be useful as a source of such components includes the Dinamap® Pro 100 blood pressure monitor, available from Woodley Equipment Company Ltd., Bolton, Lancashire, UK.

The device of the second aspect of the invention will advantageously further comprise hose or tubing between an air pump, located within the housing, and the inflatable cuff. Conventional tubing may be used for this purpose and conveniently one or more valves will be provided in the hose or tubing. Further, an electrical connection will preferably be provided between the housing and the perfusion sensor in the inflatable cuff (or other occlusion means). The electrical connection may include conventional wiring to provide electrical power to the sensor, and/or may include wiring to permit the passage of electrical signals. A convenient connector to the housing may include a USB plug/socket arrangement.

The automated apparatus of the invention typically comprises a microprocessor or microcontroller of the like which, inter alia, is preferably programmed with a curve-fitting algorithm or other modeling program to predict a minimum rate of heat loss from the perfusion sensor which might be attained during at least one occlusion of the subject's blood flow, without requiring the occlusion to be maintained until a constant and stable rate of heat loss is reached.

Preferably this curve-fitting or modeling is performed during a first or initial occlusion of the subject's blood flow by the occlusion means. The advantage of this curve-fitting or modeling is that it allows the apparatus to predict what the Emin value (see below) will be, without requiring the subject's blood flow to be occluded for 2-3 minutes, which can cause discomfort. In addition, the curve fitting or modeling decreases the response time of the apparatus (i.e. it can start to provide perfusion sensor-derived readings of blood pressure more quickly), as explained further in Example 6.

Preferably the heat flow data obtained during and/or immediately after the commencement of blood flow occlusion are disregarded or modified by the curve-fitting algorithm or other modeling program so as to allow for unwanted artefacts, again as further detailed in Example 6 below.

In a third aspect, the invention provides a method of measuring blood pressure in a subject, the method comprising the use of a device in accordance with the first aspect, or the apparatus of the second aspect, defined above and comprising the steps of:

(a) positioning the device on the subject and actuating the occlusion means at least once so as to restrict the blood flow in a portion of the subject; and (b) taking at least one reading with the perfusion sensor.

In simple terms, the method of the invention typically comprises an initial arterial occlusion (e.g. cuff inflation) in which the subject's blood pressure is calculated by conventional means by detecting Korotkoff sounds. This reading may conveniently be used to calibrate the perfusion sensor of the device of the first aspect of the invention.

Prior to the initial arterial occlusion, the rate of heat loss from the perfusion sensor is measured ("Emax"), normally in terms of mW. This value is substantially entirely caused by heat loss due to conduction into the subject's skin, and by convective losses caused by the subject's flow of blood. Typically an average value for Emax is obtained by measuring the heat loss over a period of time (e.g. a minimum of 10 seconds is usually sufficient to establish a reasonably accurate and reliable value for Emax).

When the subject's arteries are occluded, there is no longer any convective heat loss from the perfusion sensor. Accordingly, after a short delay, the heat loss from the sensor stabilises at a new, lower level (Emin), which is substantially due solely to conductive losses from the perfusion sensor. This allows calculation of the rate of heat loss due to convection (which is proportional to the rate of perfusion, which in turn is proportional to the mean arterial pressure in the subject):

$$MAP = K(Emax - Emin)$$

Thereafter, the arterial occlusion can be removed (e.g. the cuff deflated). The perfusion sensor can be used to monitor the mean arterial pressure substantially continuously, without requiring the occlusion means to be reactivated, simply by measuring the heat loss "E", as a result of the previous calibration.

Preferably the method involves taking substantially continuous readings (e.g. 1 per second or more frequently, up to as much as 100 readings per second, depending on the processor speed) with the perfusion sensor over an extended period of time (which may be, for example, from as little as 15 minutes to as much as 4 hours or more or even overnight), hence the invention provides a non-invasive method of substantially continuous monitoring of the patient's blood pressure. The frequency of cuff inflations for blood pressure readings can be adjusted according to what is appropriate in the clinical context, and may be as high as, for example, once a minute, to as little as once an hour, or anything in between. In general, in an operating theatre or emergency room, a high frequency of readings will be appropriate (e.g. one every 3-5 minutes), in an ICU or post-operative room or the like, a medium frequency (e.g. one every 5-15 minutes), and in a ward or other non-critical situation, perhaps a frequency of one reading an hour will suffice. The frequency of cuff inflations can be greatly reduced if the perfusion sensor-derived value for the subject's mean arterial pressure indicates that it is stable and within an acceptable range.

It will be appreciated that the occlusion means will not be left in a state such that blood flow in the patient is substantially restricted for prolonged periods. Thus, for example, where the occlusion means comprises an inflatable cuff, it will usually be wholly or at least partially deflated after each blood pressure reading is taken, and then re-inflated—shortly before the next blood pressure reading is due. Actuation of the occlusion means (e.g. inflation of a cuff) is conveniently automated.

The invention will now be further described by way of illustrative example and with reference to the accompanying drawings, in which.

EXAMPLES

Example 1—Principle of Operation of the Device of the Invention

Blood perfusion refers to the local blood supply per minute in a volume of living tissue, which contains a very complex mesh of blood vessels. The normal measurement unit for clinical perfusion is thus: ml(blood)/[100 g(tissue) *min].

Blood perfusion is an extremely important component of human and animal (especially mammalian) physiology. It is responsible for providing the oxygen and nutrients required by cells of the body to fuel life processes. It is also responsible for removing waste products generated by those same processes, which must be discarded to maintain the health of the system. Also, this blood flow, and the control of it, is a chief component in the thermo-regulatory system of the human body.

The significance of blood perfusion in the normal operation of the human body makes it a useful diagnostic in many areas of medical practice. The experimental use of blood perfusion sensors has been explored in many research arenas. Examples of some of the more specific fields of interest are the healing of burns and skin grafts, cerebral blood perfusion in head trauma patients, prediction of organ transplantation success before closure of the body cavity, and the detection of tumours. In each instance, researchers look for blood perfusion that differs from normal levels to determine areas of tissue damage, regions of elevated healing response, or inconsistencies in expected function.

The currently employed methods of measuring blood perfusion are either invasive, do not produce quantifiable results, or are difficult and time consuming to use (and hence impractical, especially in certain clinical contexts). Furthermore, the accuracy and repeatability of some of the measurement techniques are widely disputed.

Existing non-invasive skin tissue perfusion measurement methods depend on either infrared plethysmography, advanced optometry, CT, Mill, PET, ultrasound or laser doppler systems or washout of radioactive isotopes, which involve cumbersome or expensive equipment, specially trained staff, calibration and/or safety issues.

In an experimental setting, the "gold standard" technique for measurement of tissue perfusion is considered to be the measurement of washout of a locally-applied $^{133}$Xe isotope. However this technique is expensive, requires the use of bulky equipment, requires a high level of operator skill and, due to the use of radioactive xenon, specially trained staff and imposes safety protocols. It is clearly not suitable for routine clinical use.

The device and method of the present invention preferably involves the use of a heat flow perfusion sensor.

In essence, a heat flow perfusion sensor uses directional heat flow as the tracer agent in place of the radioactive isotope in the $^{133}$Xe washout technique. The heat flow perfusion sensor involves the establishment of a 'thermal shield' over the measurement site on the skin of the subject, to eliminate (as nearly as practical), or at least closely define, all ambient heat losses thus ensuring that heat lost from a central portion of the sensor is due substantially entirely to (i) tissue conduction and (ii) blood perfusion convection. Thus, occluding the blood flow through the tissue beneath the perfusion sensor (by actuation of the occlusion means) removes the heat loss element due to blood perfusion convection, leaving tissue conduction as the sole mechanism of heat loss. This allows a direct calculation of the tissue perfusion rate. The inventor has shown that measurements of tissue perfusion using the heat flow perfusion sensor correlate well with measurements obtained using the standard $^{133}$Xe washout technique.

A sensor suitable for use as a heat flow perfusion sensor in the device and method of the present invention is disclosed in U.S. Pat. No. 4,539,994, the entire content of which is incorporated herein by reference.

Alternatively stated, the total unidirectional heatflow (Emax) from a central thermostatted element of the skin surface is made up of two components: convection (by the flowing blood) and conduction (by the temperature gradient) in the underlying tissue. During blood flow cessation, the conductive element can be established (Emin) and the convective contribution calculated as (Emax−Emin).

Based on values for the physiological properties of blood and tissue perfusion can be calculated from this difference to provide an area perfusion measure in ml (blood)/[cm² (tissue)*min], and then, if required, scaled to correspond to the standard clinical volumetric perfusion value in ml (blood)/[100 g (tissue)*min] as measured by radioactive isotope wash-out techniques.

A simple conversion from the continuously measured perfusion value ("E") to continuous mean arterial pressure ("cMAP") can be performed according to equation 1:

$$cMAP = (E - Emin) * MAP / (Emax - Emin)$$

where: "E" is the current value of heat flow as measured by the perfusion sensor;
"Emin" is the stable heat flow level during occlusion of the subject's blood flow;
"MAP" is the mean arterial pressure reading from the BP cuff measurement (determined conventionally e.g. by detection of Korotkoff sounds);
"Emax" is the average E value obtained prior to the occlusion of the subject's blood flow This simple transformation using the heat difference (Emax−Emin) does not take into account variations in capillary temperature caused by varying actual levels of Emax, but it can still provide satisfactory cMAP monitoring traces in general clinical situations, particularly when a high frequency of repeated BP cuff inflations is available for continuous calibration.

Example 2—Detailed Description of an Embodiment

Figure 1:
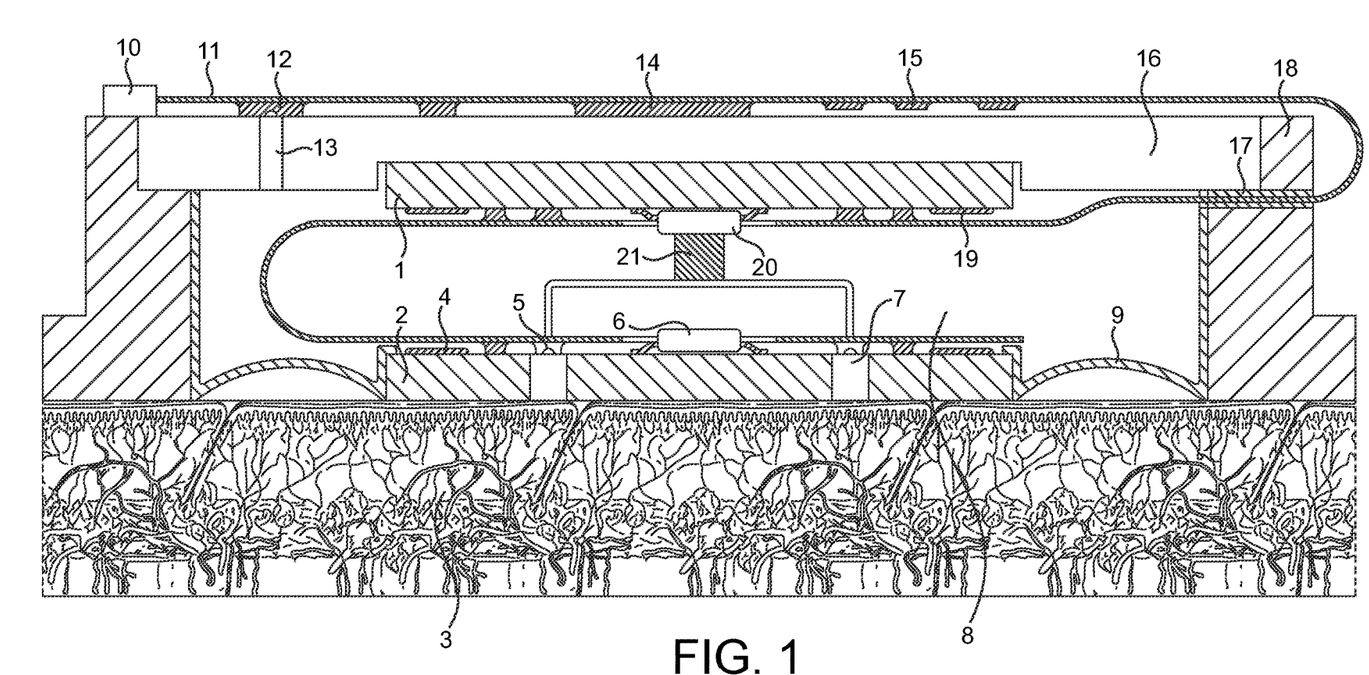
FIG. 1 is a sectional view of one embodiment of a heat flow perfusion sensor, suitable for use in the device of the invention, shown in situ above a section through human skin.

FIG. 1 shows a section through a perfusion sensor forming part of a device in accordance with the present invention, in situ on a section through human skin (3). The sensor comprises a cup-shaped metal shield formed of two parts, a lid (16) and a ring (18) designed to accommodate an upper (1) and lower (2) heat conductive substrate, which are thermostatted by means of bonded-on meandering heater elements (4, 19) and temperature sensing elements (6, 20). The upper and lower substrate (1, 2) are substantially identical, except that lower, skin-facing substrate (2) has two or more apertures or cavities (7) which are substantially filled with optically transparent light-guides, over each of which are placed one or more light sources (e.g. LEDs of differing wavelength emissions) and one or more photodetector components (5), such that the device may additionally be used to perform reflective pulse oximetry. Suitable materials for the substrates (1, 2) include, but are not limited to, aluminium oxide ($Al_2O_3$), aluminium nitride (AlN), beryllium oxide (BeO, also known as beryllia), and ceramic- or glass-coated metal disks (especially aluminium or copper disks). The space (8) between the substrates is filled with a thermal insulator such as a soft sponge structure, dry air or other inert gas. The skin-facing lower substrate (2) is resiliently deformably suspended around its rim by a flexible polymer support and sealing structure (9) that allows the assembly to keep a light but substantially constant pressure, exerted by the lower substrate (2), on the underlying skin surface (3). A second, typically similar, flexible polymer support can be optionally added between the substrates (1) and (2) to add further mechanical stability and act as an end stop to avoid excessive travel of support (21).

All electrical connections are performed by copper tracks on a flexible PCB (11), one end of which holds a connector for external cable attachment (10), a microprocessor (14) (typically soldered in place) and associated timing and power switching electronic components (15). The two substrates' connecting pads with solder bumps are soldered to matching pads on the PCB to complete the circuitry on one strip of flexible printed circuit structure.

During assembly, the PCB is fed through a cut-out in the ring-shaped part of the shield (18) before the lid (16) is pressed onto it to finish the cup-shaped shield. The upper substrate (1) is attached to a cut-out in the underside of the shield lid (16) by means of solder or an adhesive with a high thermal conductivity. The skin-facing lower substrate (2) with its polymer support (9) is bent through 180 degrees and glued into the cup structure to make a water tight seal for the resulting space (8). Any moisture is purged from the void through the narrow channel (17) and the void then filled with dry air, an inert gas or other insulator before the channel (17) is sealed with an adhesive or the like. The end of the PCB (11) is bent through 180 degrees in the other direction and attached to the top of the lid (16) by an adhesive.

The assembly also gives an option to measure the Korotkoff sounds using the lower substrate (2) operating in a similar way to a stethoscope membrane. In such an embodiment, the void is purged through a hole (13) in the lid (16) before a microphone or pressure sensor (12) is sealed over the hole (13).

The perfusion sensor in FIG. 1 is incorporated into the inner (skin-facing) surface of an inflatable cuff, (not shown in the Figure), inflation of the cuff serving to occlude blood flow through at least that part of the skin beneath the perfusion sensor.

Example 3

This example relates to a comparison of the properties of blood pressure measurement and monitoring using a device in accordance with the first aspect of the invention, and with a photoplethysmogram (PPG) prior art technique.

Referring to FIG. 2, the Figure shows the effect of lowering blood pressure under a sensor device in accordance with the invention, achieved by the subject raising their arm. This elevates the sensor site by about 60 cm, for about 55 seconds. FIG. 2 is a graph of the heat flow the sensor (measured in terms of mW) against time (minutes and seconds). The subject raised their arm at the time point marked 'A'. The subsequent trace shows that the heat flow out of the sensor decreased from about 140 mW to about 110 mW, a decrease of about 30 mW, corresponding to a calculated drop in local blood pressure of about 45 mmHg (equivalent to 60 cm water column). It can be noted that the mW trace, with the arm either raised or lowered, remains stable at the respective level corresponding to the local blood pressure. This demonstrates that the induced local skin hyperaemia (arising as a result of the local increase in temperature caused by the heated device of the invention) overrides the auto-regulatory signal 'drift' return to a baseline value, seen in PPG measurements described below.

FIG. 3A shows a graph of PPG reading (volts) against time (seconds). FIG. 3B shows the measured arterial blood pressure (mmHg against time, in seconds) for the same subject. From 0 to about 10 seconds represents the baseline. At the time point indicated by numeral 1, the subject lowered their hand, causing an increase in local blood pressure. As seen in FIG. 3A, at the time point indicated by reference numeral 2, the PPG reading shows the subject's hand fills with more blood (indicated by the higher mean value of the waveform) and that the blood vessels have become less compliant as a result of the increase in blood pressure (indicated by the decreased amplitude or "thickness" of the trace). In contrast, as seen in FIG. 3B, the amplitude of the blood pressure measurement is substantially unaltered. At the time point indicated by reference numeral 3, the hand's vascularity is starting to return towards the baseline (FIG. 3A) due to autoregulatory processes, even though (FIG. 3B) the local arterial blood pressure remains elevated.

Figure 4:
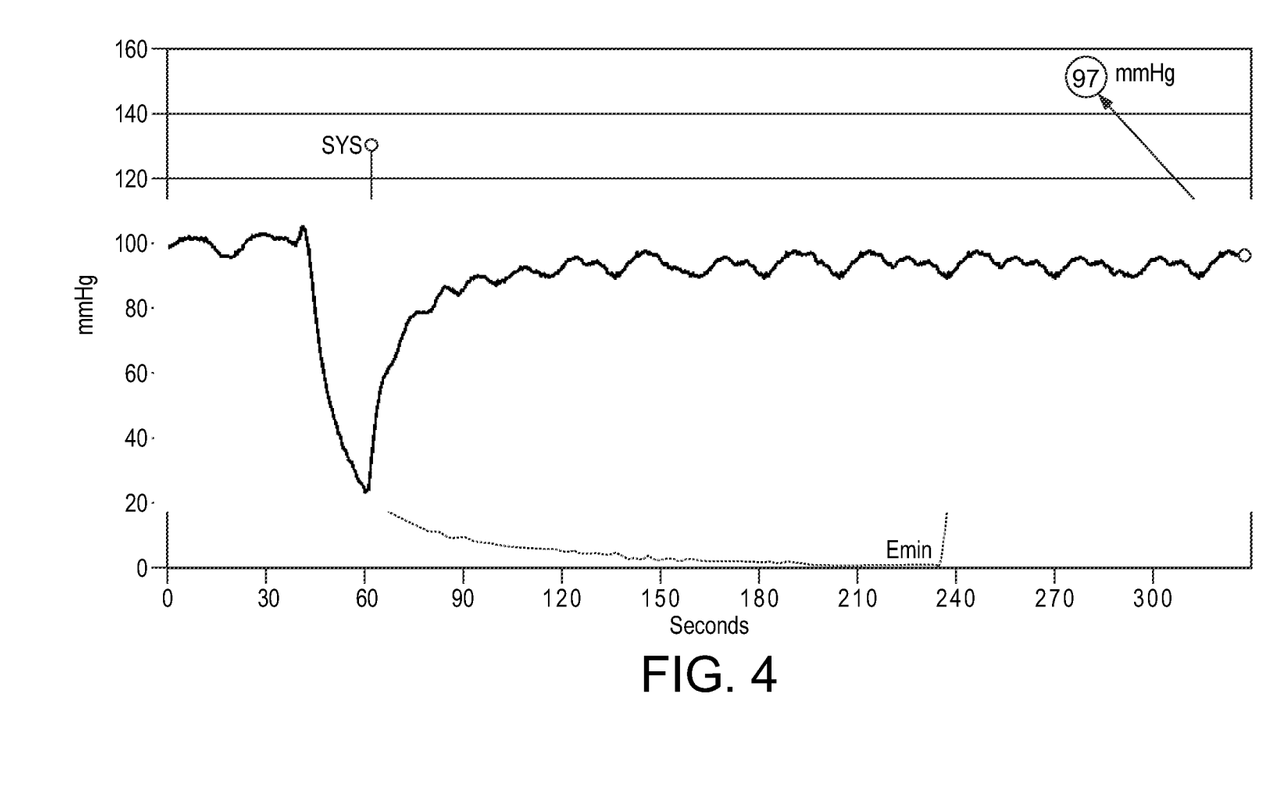
FIG. 4 is a graph of arterial pressure (mmHg) against time (seconds), showing a typical trace obtainable from a device in accordance with the invention.

Example 4—Continuous Measurement of Mean Arterial Pressure ("cMAP") Using the Device/Method of the Invention FIG. 4 shows the signal from the inventive device after its signal has already once been transformed to display BP in mmHg. It shows the continuous cMAP trace interrupted by another cuff inflation and sphygmomanometer BP measurement. The dotted line indicates how the signal would have decayed towards zero mmHg if the cuff had been kept inflated at the supra-systolic pressure. Instead, fast cropping and curve-fitting algorithms (see Example 6 below) obtain an estimate of the required Emin parameter within less than 20 seconds, upon which the cuff pressure is slowly released, as normal, to perform the sphygmomanometer BP measurement. In FIG. 4 "SYS" represents the systolic pressure, "DIA" the diastolic pressure, and "MAP" is the calculated mean arterial pressure.

As soon as this is completed and the MAP value measured (or calculated) by the sphygmomanometer device (illustrated by the vertical line in the figure), the device microcontroller reads it and also records the recent Emax values (or rather a 10-20 second average thereof) immediately prior to the cuff inflation. As performed in previous mW to mmHg transformations, using these three newly acquired variables (Emax, Emin and MAP), the device of the invention re-adjusts the scaling of the current E values according to Equation 1 to adjust and display the corresponding cMAP monitoring trace.

Example 5—Device Incorporating One or More Additional Sensors

One drawback of the heat washout principle is that it is limited by the relatively slow thermal clearance rate of the measured skin volume and thus cannot produce the pulsatile blood pressure waveform of the photoplethysmogram (PPG) or Doppler-based intra-arterial pressure systems.

However, it does provide a stable and reliable cMAP baseline readout based on an absolute measurement of local perfusion, which both the PPG and Doppler systems lack. Further, the present device design offers opportunities to incorporate standard PPG and/or doppler light source(s) and receiver(s) into one integrated unit. Further, integrating two different light sources and one receiver enables the measurement of arterial oxygen saturation through reflective pulse oximetry (spO2).

These PPG or Doppler-based sensors may be incorporated into the device of the first aspect of the invention, more especially into an inflatable cuff. In particular they may be integrated with the perfusion sensor (e.g. controlled by the same microprocessor or microcontroller which operates and controls the perfusion sensor).

Combining these sensor principles gives the opportunity to provide not only a calibrated cMAP as described above, but using the systolic and diastolic information from the BP cuff measurement to scale the PPG waveform to give a readout of non-invasive, continuous systolic and diastolic arterial pressure information to provide a full continuous Arterial Blood Pressure readout—as well as spO2 and pulse rate. Again, the hyperaemia below the sensor helps improve the signal/noise ratio and reduce the known respiratory, venous pulsation and movement artefacts of these additional measurements.

Example 6—Improved Response Time

The relatively slow thermal clearance rate also poses a practical clinical issue in that the time required to determine the Emin (the baseline conductive heat loss without blood flow) is about 3 minutes. This is problematic because for the patient to have a cuff inflated to supra-systolic pressure for several minutes is undesirable and uncomfortable, and secondly the intended continuous cMAP monitoring is effectively suspended during that time.

Therefore, another preferred feature of the invention is that this measurement period can be shortened significantly as the cuff occlusion response of the sensor can be well-defined and can be predicted by a curve-fitting algorithm based on very few initial signal decay data.

Even though most physiological response systems are inherently exponential in nature (as is indeed the mW signal of the inventive device), it is suggested to approximate the decay by other models based on arithmetic models (e.g. Saturation-Growth, Hoerl, Root Fit or MMF models etc.) which require significantly less processor calculation effort and provide much faster curve fitting results from an inexpensive microcontroller device. This, in turn, allows for abbreviated supra-systolic cuff inflations while still providing satisfactory clinically accurate results.

Figure 5:
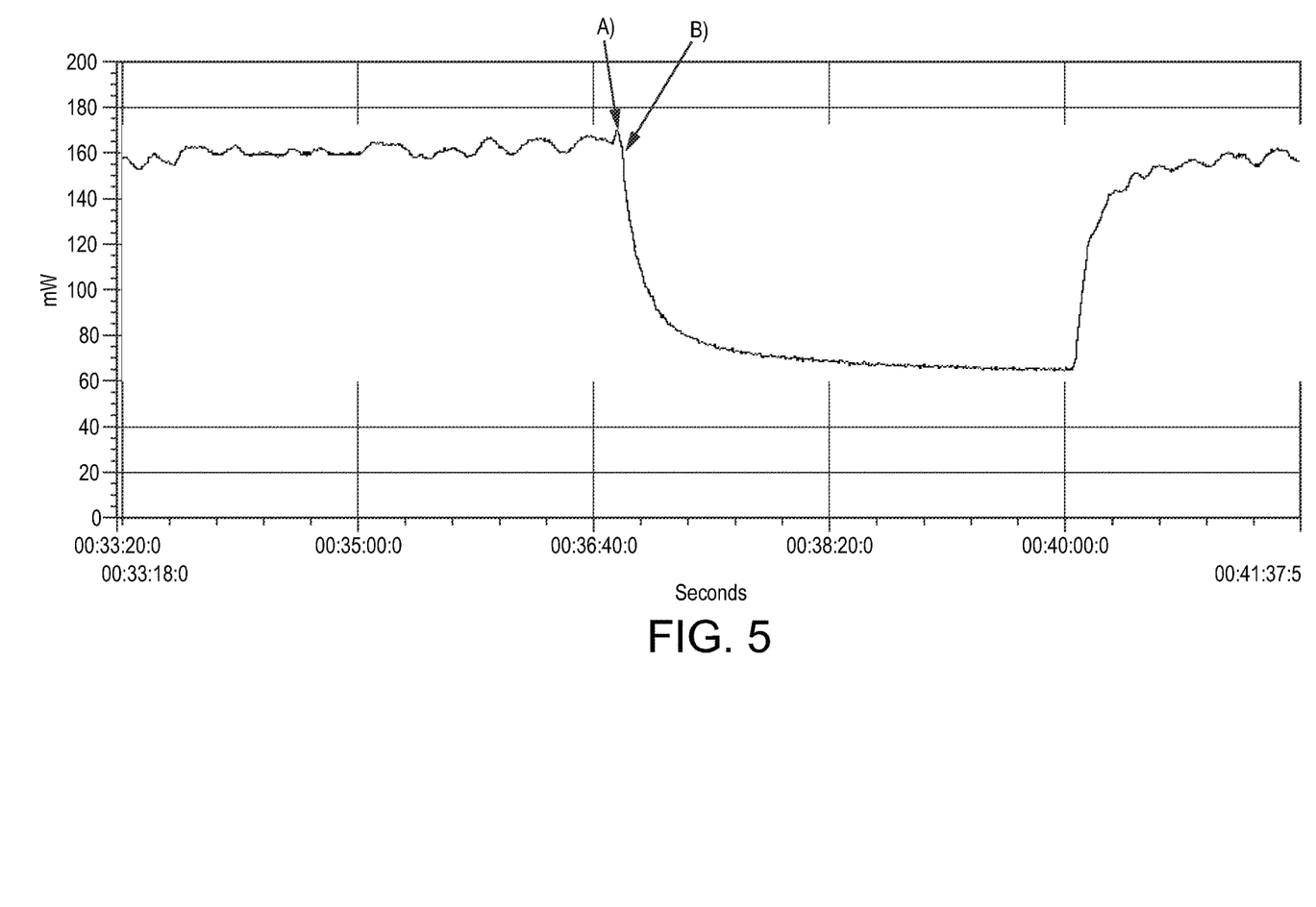
FIG. 5 is a graph of perfusion sensor signal (in mW) against time (seconds) obtained using the device of the invention, showing the mW signal decay response from Emax to Emin during a cuff inflation, including the initial decay artefacts caused by the common non-ideal initial arterial occlusion by the pneumatic cuff inflation.

Referring to FIG. 5, the initial decay signal from the time point at which the cuff is inflated may contain unwanted artefacts. In the Figure, (A) denotes a brief local BP increase due to the pressure transient from a quick cuff inflation, and (B) indicates is a "waterfall" rounding effect (often due to a slow cuff inflation) where the arterial bloodflow cut-off is not instantaneous. These effects will disturb any curve-fitting or predictive model, and should be omitted or "cropped" from the curve-fitting data set.

Figure 6:
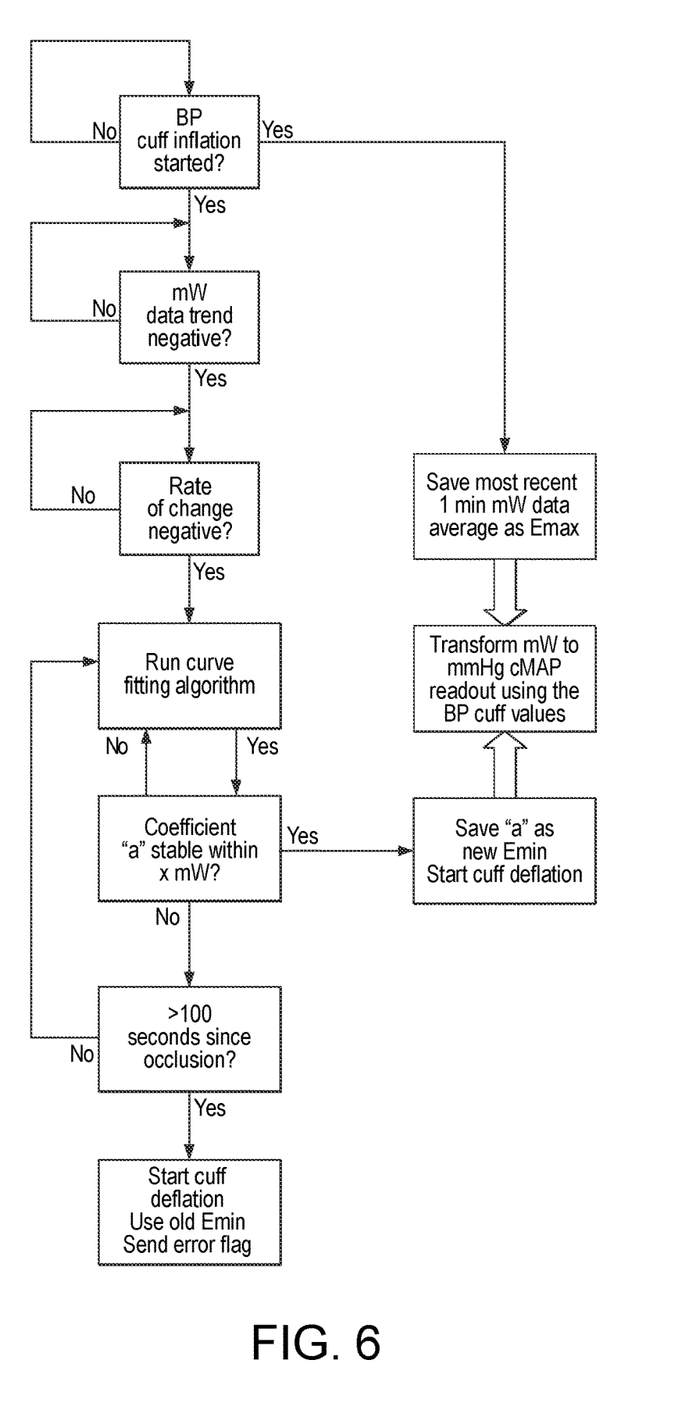
FIG. 6 shows a flow chart for an algorithm that may be used to 'crop' the initial decay artefacts illustrated in the trace in FIG. 5, providing a faster response time for the device of the invention.

Cropping can be performed in one embodiment by simply ignoring data from a set amount of seconds after the commencement of cuff inflation. However, it is proposed that a continuous real-time signal analysis is performed on the signal decay to better and more quickly eliminate these initial effects by establishing the point when the decay is monotonous and negative—and when the rate of decay becomes negative, establishing the tangent at this point and starting the curve fitting process from that point. Then, continuously running a curve fitting algorithm during the following signal decay to establish the point when the end value predictions are within an acceptable +/−x mW level (x typically being in the 2-4 mW range, reflecting the desired accuracy), by which the supra-systolic cuff inflation can be ended at the earliest possible time. The process is shown in the flow chart of FIG. 6.

Using a Saturation-Growth model y=a*t/(b+t), the curve-fit parameter "a" directly gives the stable end-value Emin, because lim(y)=a as t goes to infinity. http://pundit.pratt.duke.edu/wiki/MATLAB:Fitting The following table 1 shows the end value predictions during a supra-systolic occlusion period based on data available from 20 seconds to 180 seconds after adaptive cropping of the first 6-10 seconds of measurement including artefacts:

TABLE 1

End-value coefficient estimates from repeated curve fitting
using a Saturation-Growth model y = a * t/(b + t)
using data available from 20 to 180 seconds after initial
data cropping. All curve fits converged to a tolerance of
1e-006 in less than 5 iterations with r values over 0.99.

| Time [sec] | 20 | 40 | 60 | 90 | 120 | 180 |
|---|---|---|---|---|---|---|
| Coefficient "a" estimate [=Emin in mW] | 60.6 | 62.1 | 62.9 | 63.3 | 63.3 | 63.2 |
| Coefficient "b" estimate | −9.4 | −9.0 | −8.7 | −8.6 | −8.6 | −8.6 |

This cropping allows a cMAP monitoring trace with less than 20-30 second interruptions in conjunction with normal cuff inflations, giving a substantially continuous ambulatory BP display in all practical clinical settings. Further, if the cMAP trace stays stable, the next "programmed" cuff inflation (according to the pre-determined time interval) can be postponed, giving the patient less inconvenience—or conversely, if the cMAP signal should suddenly drop, the upcoming BP cuff inflation measurement can be brought forward to determine the cause and act as an improved patient circulatory status safeguard.

Example 7—Perfusion Sensor Placement for Obtaining Best Curve-Fit

Figure 7:
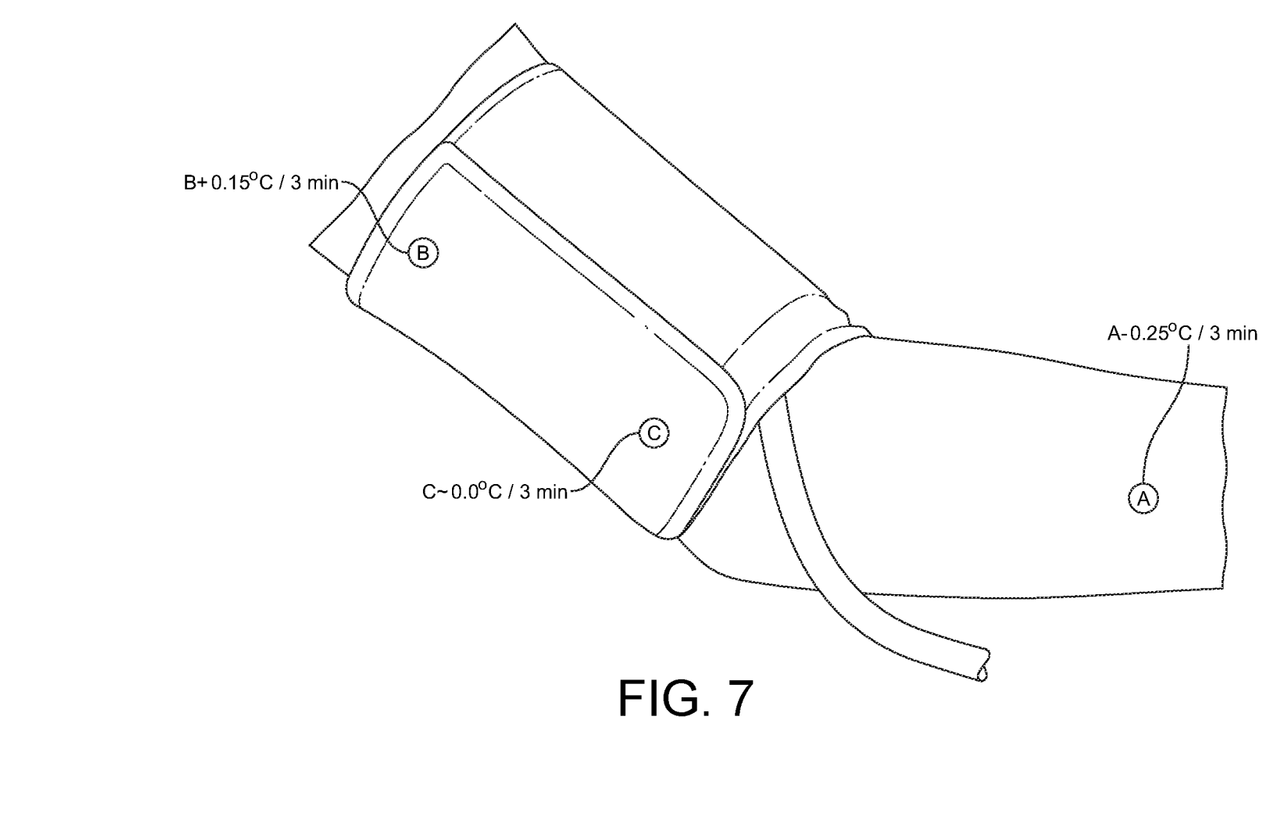
FIG. 7 is a representation of one embodiment of a device in accordance with the invention in situ on a human subject's arm, with the preferred location of the perfusion sensor indicated by letter "C"

One further advantage of applying a quick, early prediction of the arterial-occluded heat clearance rate is that the leg or arm internal temperature level is affected by a lengthy cuff cessation of the blood flow. Distal to the cuff, uncovered, and at 21° C. ambient temperature, a human arm core cools down by approx 0.25° C. over 3 minutes (shown at position 'A' in FIG. 7). Conversely, the core temperature proximal (i.e. "upstream"), or directly under, the BP cuff increases by approx 0.15° C. due to the lack of cooling venous blood return (shown at position 'B' in FIG. 7). While these changes in "base level" cause a marginal 3-4% error in an absolute perfusion measurement, any moving end value target does influence the curve-fitting algorithm consistency, and it is therefore suggested that an optimal placement of the heat clearance sensor is directly distal to the inflatable bladder in the BP cuff (shown at position 'C' in FIG. 7) where the effective internal temperature change approaches zero over the cuff inflation duration—and movement artefacts are reduced compared with placement on lower extremities.

Example 8

Figure 8:
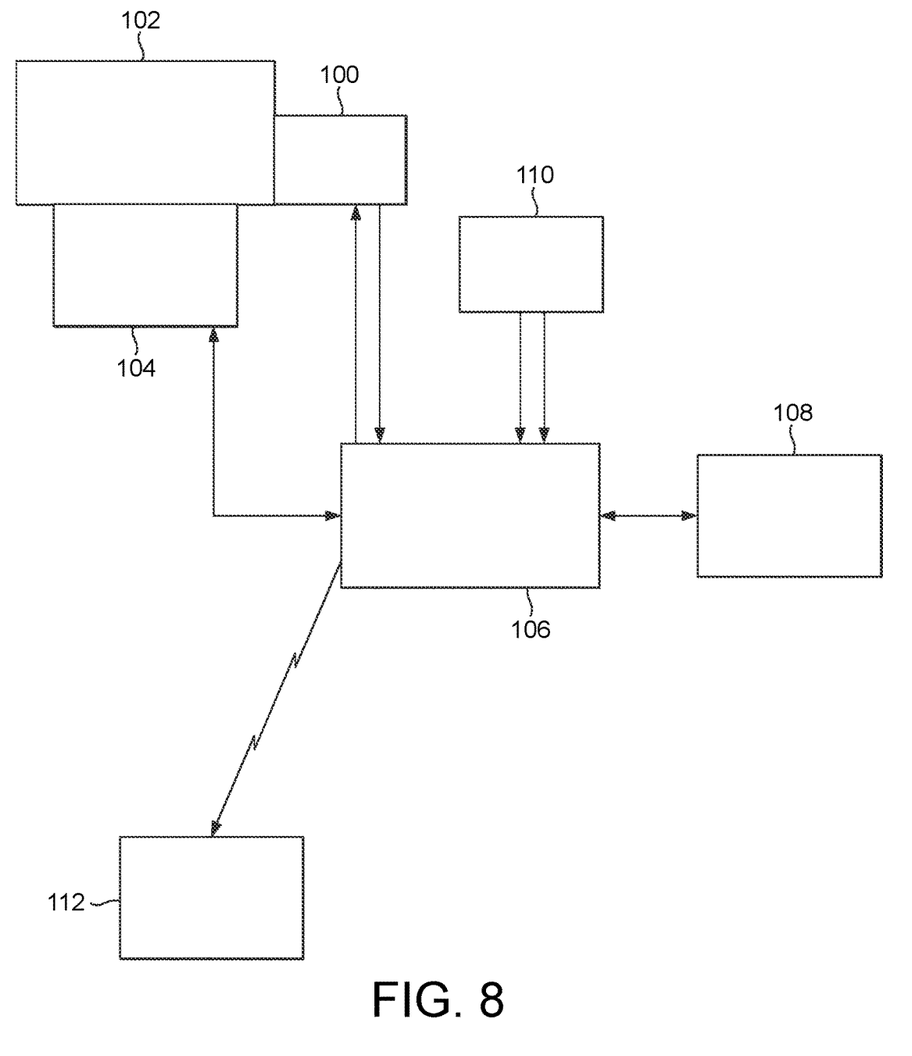
FIG. 8 is a schematic illustration of an embodiment of automated apparatus in accordance with the second aspect of the invention, comprising a device in accordance with the first aspect.

A schematic illustration of one embodiment of an automated system or apparatus in accordance with the second aspect of the invention is shown in FIG. 8.

Referring to FIG. 8 the apparatus comprises a heat flow perfusion meter/sensor device 100 in accordance with the first aspect of the invention. The heat flow perfusion meter/sensor device is typically substantially as shown in FIG. 1 and as described in Example 2 above. The meter/sensor device 100 is incorporated within an occlusion means 102, which comprises an otherwise conventional inflatable cuff. The cuff is adapted and configured to be positioned around the arm of a typical adult human and, when inflated, can cause occlusion of the blood vessels in the arm. The occlusion means is operably connected to an actuation means 104, which typically comprises a pump of a conventional sort. The actuation means 104 may be directly attached to the occlusion means 102, or may be remotely situated and operably connected thereto by means of, for example, air tight tubing.

The perfusion meter/sensor device 100 and the actuation means 104 are under the control of a digital electronic control apparatus 106. Signals between the device 100 and the control apparatus 106 and between the actuation means and the control apparatus 106 may be transmitted electrically by a wired connection, or may be transmitted by a wireless communication means such as Bluetooth, NFC or the like.

The digital control apparatus conveniently comprises a computer or microprocessor and is provided with a power source 110. The power source 110 preferably provides electrical power. The power source 110 may be integral to the control apparatus, or may be external (e.g. a connection to a mains electrical supply). In some embodiments the apparatus may comprise both an integral power supply (e.g. one or more batteries) and a connection to an external power supply.

The control apparatus is operably connected to a monitor or display such as a conventional computer monitor. The monitor may display useful information relating to, for example, the measured perfusion of the subject, the subject's continuous mean arterial pressure, pulse rate etc. The monitor may also display information as to the operational status of the apparatus, error messages etc. The monitor preferably also includes a visual alarm indication in the event that a measured patient parameter (perfusion rate, or cMAP) falls outside an acceptable range. The apparatus may also provide an audible alarm in such an eventuality.

Desirably the control apparatus is also operably connected to a remotely-situated visual and/or audible alarm 112. Such a remotely-situated alarm 112 may advantageously be located, for example, at a nurses' station or the like on a hospital ward. Operable connection to such a remotely-situated alarm 112 may be via a wired connection or, as indicated in FIG. 8, by means of wireless communication.

Where there are several different control apparatus 106 operably connected to a single common, centralised remotely-situated alarm, the different control apparatus 106 may include an identification signal or the like when transmitting an alarm signal to the remote alarm 112, so that the nursing staff can tell which control apparatus 106 has generated the alarm.

The invention claimed is:

1. A blood pressure measurement device comprising:
   a heat flow perfusion sensor; and
   a microprocessor;
   the heat flow perfusion sensor configured to calculate perfusion from measuring heat loss due to convection by blood flow in a human subject or animal body;
   the heat flow perfusion sensor in integral combination with an occlusion means for restricting flow of blood in a portion of the human subject or animal body;
   the heat flow perfusion sensor comprising: an outer portion and an inner portion wherein the inner portion is resiliently deformable, and the inner portion is configured to enable relative movement of the inner portion with respect to the outer portion;
   the microprocessor operatively connecting to the blood pressure measurement device and configured to perform a curve-fitting algorithm or other modeling program to predict a minimum rate of heat loss from the perfusion data which is attained during at least one occlusion of the blood flow in the human subject or animal body, without requiring the occlusion to be maintained until a constant and stable rate of heat loss is reached and wherein the microprocessor further configured to calculate blood pressure of the human subject or animal body based in part on the minimum rate of heat loss.

2. The blood pressure measurement device of claim 1, wherein the occlusion means comprises an inflatable cuff.

3. The blood pressure measurement device of claim 1, comprising at least one heating means, which is configured, in use, to heat skin of the human subject or animal body that is in contact with the blood pressure measurement device to a temperature in excess of a normal skin temperature for the human subject or animal body.

4. The blood pressure measurement device of claim 1, wherein the inner portion is resiliently deformable because the inner portion is mounted on a resiliently deformable polymeric film.

5. The blood pressure measurement device of claim 4, wherein the outer portion comprises an annular outer portion.

6. The blood pressure measurement device of claim 1, comprising a microphone or other electrical acoustic sensor configured to detect Korotkoff sounds and to provide a measurement of the blood pressure in the human subject or animal body.

7. The blood pressure measurement device of claim 6, configured to use the blood pressure measurement so obtained to calibrate readings of the heat flow perfusion sensor.

8. The blood pressure measurement device of claim 6, wherein the occlusion means is an inflatable cuff and the microphone or other electrical acoustic sensor is located within the inflatable cuff, or is remotely located but in fluidic connection with the inflatable cuff.

9. The blood pressure measurement device of claim 1, further comprising a thermostat or other temperature control means.

10. The blood pressure measurement device of claim 1, further comprising a sensor which performs a photoplethysmogram blood pressure pulse wave analysis of the human subject or animal body and/or a sensor which performs pulse oximetry analysis of the human subject or animal body.

11. The blood pressure measurement device of claim 1, wherein the heat flow perfusion sensor is located under the occlusion means and positioned in a thermally neutral location when the blood flow in the human subject or animal body is occluded.

12. The blood pressure measurement device of claim 1, wherein the microprocessor is operably connected to actuate the occlusion means at a predetermined time interval and to actuate the occlusion means when blood pressure in the human subject or animal body, as determined by the heat flow perfusion sensor, falls outside a predetermined acceptable range.

13. The blood pressure measurement device of claim 1, wherein the curve-fitting algorithm or other model program predicts a minimum rate of heat loss during an initial occlusion of blood flow in the human subject or animal body.

14. The blood pressure measurement device of claim 1, wherein heat flow data obtained immediately after commencement of blood flow occlusion are disregarded or modified by the curve-fitting algorithm or other modeling program to omit unwanted artifacts.

15. A method of using the blood pressure measurement device of claim 1 for measuring blood pressure in the human subject or animal body, the method comprising the steps of:

(a) positioning the blood pressure measurement device on the human subject or animal body and actuating the occlusion means at least once to restrict the blood flow in a portion of the human subject or animal body; and (b) taking at least one reading with the heat flow perfusion sensor.

16. The method of claim 15, further comprising the step of operating the heat flow perfusion sensor to provide a substantially continuous reading of blood pressure in the human subject or animal body.

17. A method of using the blood pressure measurement device of claim 1, comprising the steps of detecting an abnormal circulatory condition in the human subject or animal body by attaching the blood pressure measurement device to the human subject or animal body; and using the blood pressure measurement device to monitor circulation in the human subject or animal body.

18. The method of claim 17, further comprising the step of continuously monitoring of mean arterial pressure in the human subject or animal body.

19. The method of claim 17, further comprising the step of detecting circulatory shock or sepsis in the human subject or animal body.

* * * * *